United States Patent
Fridman et al.

(10) Patent No.: US 7,466,148 B2
(45) Date of Patent: Dec. 16, 2008

(54) SENSOR SYSTEM FOR MEASURING AN ELECTRIC POTENTIAL SIGNAL OF AN OBJECT

(75) Inventors: Igor Fridman, San Diego, CA (US); Paul Hervieux, San Diego, CA (US); Linas Kunstmanas, Valley Center, CA (US); Robert Matthews, San Diego, CA (US)

(73) Assignee: QUANTUM Applied Science & Research, Inc., San Diego, CA (US)

( * ) Notice: Subject to any disclaimer, the term of this patent is extended or adjusted under 35 U.S.C. 154(b) by 239 days.

(21) Appl. No.: 10/591,344

(22) PCT Filed: Jul. 1, 2005

(86) PCT No.: PCT/US2005/023606
§ 371 (c)(1),
(2), (4) Date: Aug. 31, 2006

(87) PCT Pub. No.: WO2006/007573
PCT Pub. Date: Jan. 19, 2006

(65) Prior Publication Data
US 2007/0135701 A1 Jun. 14, 2007

Related U.S. Application Data

(60) Provisional application No. 60/584,146, filed on Jul. 1, 2004.

(51) Int. Cl.
*G01R 27/26* (2006.01)
(52) U.S. Cl. ...................... 324/686; 324/658
(58) Field of Classification Search ............ 324/658, 324/686, 72, 76.11; 600/382
See application file for complete search history.

(56) References Cited

U.S. PATENT DOCUMENTS

| | | | |
|---|---|---|---|
| 4,804,922 | A | 2/1989 | Sometani et al. |
| 5,001,440 | A | 3/1991 | Zerod |
| 5,191,891 | A | 3/1993 | Righter |
| 5,632,280 | A | 5/1997 | Leyde et al. |
| 5,650,750 | A | 7/1997 | Leyde et al. |
| 6,411,108 | B1 | 6/2002 | Douglas et al. |
| 6,438,406 | B2 | 8/2002 | Yonce |

(Continued)

FOREIGN PATENT DOCUMENTS

WO WO 01/16607 3/2001

(Continued)

OTHER PUBLICATIONS

Horowitz and Hill, "The Art of Electronics", second edition, p. 266 1989, no month's available.

*Primary Examiner*—Vincent Q Nguyen
(74) *Attorney, Agent, or Firm*—Diederiks & Whitelaw, PLC

(57) ABSTRACT

The invention generally pertains to reducing artifact noise signals present when non-invasive capacitive-type signal measurements are taken of static electric fields produced by an object of interest. According to a first preferred embodiment of the invention, a given static artifact signal is reduced by minimizing the potential difference between a ground point of sensor circuitry and the potential of the object. According to a second preferred embodiment of the invention, the change in signal due to motion of the sensor in the field produced by the object is minimized by reducing the impact of changes in coupling to the signal source.

17 Claims, 6 Drawing Sheets

U.S. PATENT DOCUMENTS

| | | |
|---|---|---|
| 6,472,888 B2 | 10/2002 | Oguma et al. |
| 6,611,168 B1 | 8/2003 | Denison et al. |
| 6,686,800 B2 | 2/2004 | Krupka |
| 7,088,175 B2 | 8/2006 | Krupka |
| 2002/0038092 A1 | 3/2002 | Stanaland et al. |
| 2004/0070446 A1 | 4/2004 | Krupka |
| 2004/0073104 A1 | 4/2004 | Brun Del Re et al. |

FOREIGN PATENT DOCUMENTS

| | | |
|---|---|---|
| WO | WO 02/065904 | 8/2002 |
| WO | WO 02/065905 | 8/2002 |

SENSOR SYSTEM FOR MEASURING AN ELECTRIC POTENTIAL SIGNAL OF AN OBJECT

CROSS-REFERENCE TO RELATED APPLICATION

The present application represents a National Stage application of PCT/US2005/023606 filed Jul. 1, 2005 entitled "A Sensor System for Measuring an Electric Potential Signal of an Object", and claims the benefit of U.S. Provisional Patent Application Ser. No. 60/584,146 filed Jul. 1, 2004 entitled "Method to Reduce the Effect of Static Potentials in Capacitive Measurements.

STATEMENT OF GOVERNMENT INTEREST

The United States Government retains a royalty fee, fully paid up, non-exclusive license to make, use, have made, or have the invention used for governmental purposes.

BACKGROUND OF THE INVENTION

1. Field of the Invention

The present invention pertains to measuring an electric potential signal generated by an object and, more particularly, to reducing the effect of artifact signals or signals caused by a change in static potential on measurement of an electric potential signal of interest.

2. Discussion of the Prior Art

Capacitive electrodes that sense the electrical potential produced in the space surrounding a voltage source enable many important new measurement modalities. For example, a particularly important new capability is the measurement of bioelectric signals, such as those measured during an electrocardiogram (ECG) or an electroencephalogram (EEG), without touching a subject's skin. In such cases, signals of interest, such as those produced by a heart or brain, are measured. An arrangement for making such measurements is set forth in U.S. Pat. No. 6,686,800 which is hereby incorporated by reference. While the system set forth in the '800 patent is effective, almost all capacitive measurements that occur in real world environments are degraded by artifact signals and noise caused by the presence of static electric fields.

Static electric fields are everywhere. An important limiting factor in capacitive measurements is the behavior of static electric potential in the region where sensors must be located to measure a signal of interest. If ambient static potentials where truly static and never changed, they could not be measured by sensors using a capacitive electrode arrangement. However, the static potential on a measured object changes for various reasons. For example, the static potential level may rise dramatically due to triboelectric charging and reach levels on the order of 10,000V. Further, the static potential can vary significantly due to discharging and the influence of other conducting bodies. In addition, motion of a capacitive sensor relative to the static electric field produces a change in the potential that is sensed. Such changes in the sensed potential can saturate the capacitive electrode causing large changes in the output signal produced by the sensor. Even at low levels, changes in the static electric field will appear as measured unwanted artifact signals. Such artifact signals can often be very similar in frequency to the signal of interest and thus are typically very difficult to filter.

In the case of a sensed bioelectric signal, certain artifact signals, such as common mode signals, can be particularly troublesome. Often, common mode signals are of low frequency and can be read as a heartbeat. Such a state of affairs can lead to the measuring equipment reading a normal heartbeat when, in fact, the heartbeat is not normal. The opposite is also true and can lead to measuring equipment reading an irregular heartbeat or fibrillation when the heartbeat is actually normal. One solution to this problem is suggest by Leyde et al. in U.S. Pat. No. 5,650,750 which is hereby incorporated by reference. Leyde et al. simply propose a way to measure faults. To this end, in the Leyde et al. arrangement, common mode voltage signal is measured and identified. However, no simple way of eliminating such signals is proposed.

In the case where an electric potential is measured through a more common resistive type coupling in which a low-impedance electrical contact is made with the object of interest, the static potential on the object is relatively easy to control. Typically it is controlled with a simple additional electrical connection to the object. For example, an electrocardiogram (ECG) taken in a hospital involves electrodes that attach to a patient's skin via a gel or adhesive that make electrically conducting connections with the patient's body. With such an arrangement, it is relatively simple to discharge static electricity by using an additional resistive contact ground strap, or even to use the electrodes themselves. However, the main idea behind using capacitive electrodes is to measure signals in a noninvasive manner. Since, by its very nature, a non-invasive capacitive measurement system cannot make a resistive coupled electric contact with an object, in such a system, a static potential cannot be reduced in this manner.

One proposed method to facilitate capacitive measurement is to allow an entire measurement system to float at the potential of the object. Such an approach is designed to minimize the absolute potential presented to the sensor relative to the remainder of the sensing system. However, this approach is limited by how similar the potential of the sensing system is to the static potential of the object. For a measuring system that is only connected to an object of interest by a capacitive coupling, the measuring system's potential is always different from that of the object, thereby producing a potential difference across the sensing region that could still be rather large compared to the signal of interest.

Yet another proposed solution to reducing signal artifacts when using capacitive measuring to sense a voltage signal of interest is to use two or more capacitive electrodes and subtract their outputs. Taking the difference of the two sensor measurements is standard practice in many applications. For example, the lead configurations used to diagnose heart ailments in an ECG have such a configuration. So long as the static potential does not exceed the measurement range of the sensors, the effect of such static potential can be removed for a large extent by taking the difference between two or more sensor inputs. Such an approach works relatively well for conventional skin contact resistive electrodes but does not work so well for capacitive electrodes, particularly ones that are not firmly attached to the body.

A capacitive-based system requires measuring a relatively small signal of interest, such as a heartbeat, against the background of much larger signals. Essentially, a small signal would have to be determined by subtracting the measured value of two or more relatively large static potential signals. This type of measurement would be limited by the unknown variations in the coupling of each sensor to the static potential, the calibration precision of the sensor components, and the dynamic range of the differencing system. The calibration precision of the sensor components and the dynamic range of the differencing system can be improved through increased complexity of the measuring system and increased cost associated with improving the quality of the measuring system's parts. However, the unknown variations of the coupling of each sensor is a fundamental problem for capacitors in a static electric field. Of course, the variations in coupling to the static electric potential can be minimized by positioning the sensors firmly against the measured object. However, such an approach is not compatible with non-invasive measuring. For example, such a technique would not work with sensors located in clothing.

There is inherently a lack of precision and repeatability in the coupling efficiency of a capacitive sensor to the static potential due to changes in the capacitance electrode that couples to the potential. If the fraction of the static signal coupled to two different types of sensors is different, then subtracting their outputs will not cancel the static signal even if the sensors are identical. The variation in coupling efficiency can be understood by the following example. Say a signal presented at the input of a first stage amplifier of a capacitor sensor is determined by a potential divider network comprised of an electrode capacitance and an input capacitance of an amplifier. On a human body, variations in the electrode capacitance can occur due to variations in the thickness of the outer skin layer, variations in the thickness of the clothing between the electrode and the subject, and a relative motion between the electrode and the subject.

Based on the above, there exists a need in the art for a system that is able to reduce the effect of a background static electric field when making high-sensitivity capacitive measurements of the electric potential in the vicinity of an object of interest, while not interfering with the overall goals of a non-invasive measuring system. Another aspect of the invention is to make the signal measured by a capacitive electrode less susceptible to the differences in electrode capacitance.

SUMMARY OF THE INVENTION

The invention generally pertains to reducing artifact noise signals that are generally present when non-invasive capacitive type measurements are taken of a body. More specifically, the invention pertains to reducing the artifact signals measured by a capacitive sensor when the sensor is operated in a static electric field produced by an object of interest. According to a first preferred embodiment of the invention, a given artifact signal can be reduced by minimizing the potential difference between a sensor circuit ground point and the potential of the object. According to a second preferred embodiment of the invention, the change in signal due to the sensor's motion in the field produced by the object is minimized by reducing the impact of changes in coupling to the signal source.

The invention generally includes a sensor system for measuring an electric potential signal generated by an object. A first signal sensor is provided including a capacitive-type electrode and an amplifier with a DC supply, a local ground connection, an input connected to the capacitive-type electrode and an output sending a signal. A second signal sensor is provided including a capacitive-type electrode and an amplifier with a DC supply, a local ground connection, an input connected to the capacitive-type electrode and an output sending a signal. A differential amplifier, including a first input connected to the output of the first signal sensor and a second input connected to the output of the second signal sensor, has an output sending a signal of interest proportional to the difference between the signal of the first signal sensor and the signal of the second signal sensor. Processing circuitry includes an input connected to the output of the differential amplifier and a local ground connection. A ground sensor includes a first ground electrode, a second ground electrode, and an amplifier with a DC supply. A ground connection is attached to the first ground electrode and a universal ground. An input is connected to the second ground electrode and an output is connected to the ground connection of the amplifier of the first signal sensor and the amplifier of the second electrode. By this arrangement, a voltage present at the local ground connections of the first and second signal sensors is forced to be the same as the voltage present at the second ground electrode so as to reduce an effect of a change in static potential on the signal of interest.

In another embodiment, a capacitor is inserted in series between the electrode and the amplifier of the first signal sensor, while the electrode of the first signal sensor and the body are separated by a relatively large distance. In yet another embodiment, the electrode of the first signal sensor and the body are connected by an electrically conducting fluid. In a still further embodiment, a feedback network including an amplifier and a series capacitor are included. The gain of the amplifier in the feedback circuit is set to 1 plus the input capacitance of the high impedance amplifier connected to the electrode, including other stray capacitances in the system, divided by the value of the series capacitor of the feedback network. Such an arrangement will produce a negative capacitance that will compensate for not only the capacitance between the amplifier and ground but also other stray capacitance present in the system.

Additional objects, features and advantages of the present invention will become more readily apparent from the following detailed description of preferred embodiments when taken in conjunction with the drawings wherein like reference numerals refer to corresponding parts in the several views.

DETAILED DESCRIPTION OF THE PREFERRED EMBODIMENTS

Figure 1:
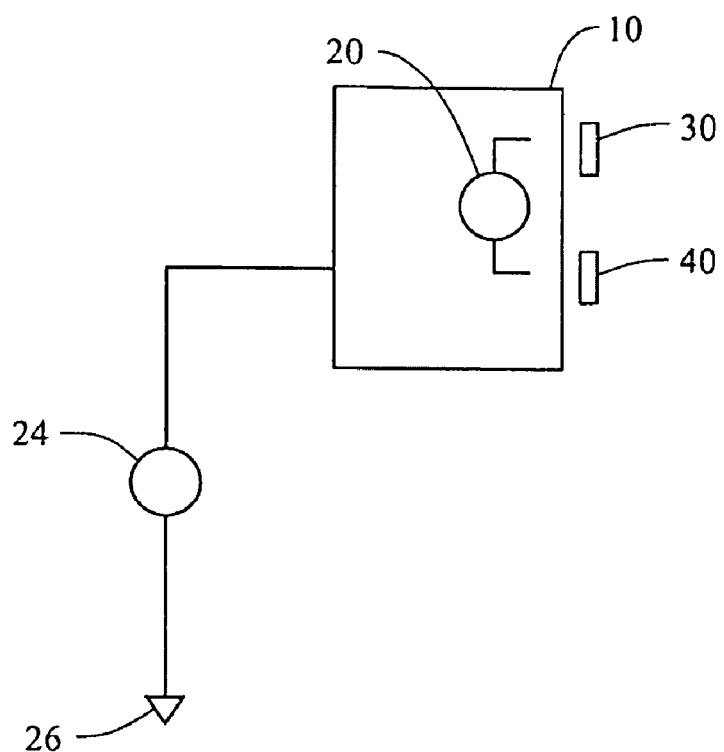
FIG. 1 is a schematic diagram showing the measurement of a signal of interest originating from a body.

The overall system for measuring a signal can be generally discussed with reference to FIG. 1. An object or body 10 has a source 20 of alternating current type voltage located therein. This voltage source 20 produces a voltage signal of interest that is to be measured. Object 10 is large compared to the spatial variation of the signal of interest produced by voltage source 20. Object 10 is charged to a static potential 24 relative to a distant point which we will define as a ground 26 having a voltage or potential of zero. The conductivity of object 10 is such that the static potential 24 at its surface 27 is substantially uniform compared to the spatial variation of the signal of interest. Further, object 10 maintains this spatial uniformity over the timescales of interest even when the static potential 24 suddenly changes. An example of such an object would be an aircraft, a human body, or a partly conducting shield placed over a sensor to protect it from the environment. Source 20 for the signal of interest could be inside object 10. For example, in the case of a human body, the heart may be source 20 of the signal of interest. Although not shown, the signal could also be produced outside object 10. For example, the source could be the field created by a moving projectile.

One or more capacitive sensors 30 and 40 are located sufficiently close to object 10 such that the magnitude of the influence of the static potential at the point of measurement is comparable to the signal of interest. Sensors 30 and 40 can be located adjacent to each other at approximately the same distance from object 10 as shown in FIG. 1 or in-line with each other in a direction normal to the object's surface 27 as shown by reference numerals 30' and 40' in FIG. 2. At this point it should be realized that other combinations of the two arrangements for the sensors 30 and 40 could also be employed.

The large, almost constant electrical potential present on the object 10 is referred to as electrical static potential 24. The charge is usually produced by a triboelectric phenomena. Electrical static potential 24 is extremely large in comparison to the signals of interest in most applications. Indeed, static potential 24 can easily be greater than 10,000 V, but the signal of interest may only be on the order of 1 μV to 1 mV. A true capacitive sensor will not actually measure static potential 24 directly because a DC current provides no reading in a capacitive sensor as the transfer function goes to zero when sensed voltage is not oscillating. However, changes in the static potential due to tribocharging or a change in the capacitance of object 10 relative to ground 26 can be measured and may be greater than the maximum input range of measurement electronics incorporated into a sensor system 28, such as shown in FIGS. 3 and 4, which is typically less than 10V.

While a sensor system 28 of the present invention may by used in many different environments, for convenience, it will be described in relation to the case of measuring a biological potential, such as performing an electrocardiogram or electroencephalogram on human body object 10. Of course, it will be appreciated that the present invention applies to cases in which one desires to minimize the effect of a large static potential 24 on a sensitive measurement taken in a minimally invasive manner.

Figure 2:
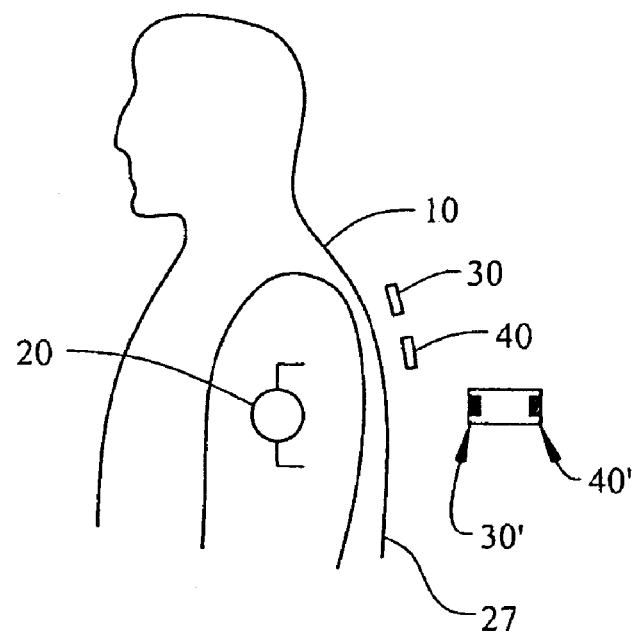
FIG. 2 is a schematic diagram showing the measurement of a signal of interest originating from within a human body using capacitive sensors, each of which is spaced from the body.

With reference to FIG. 2, there are shown four capacitive sensors 30, 40, 30', 40' positioned in proximity to human body object 10. Preferably, sensors 30, 40, 30', 40' employ a capacitive coupling to sense voltage source 20 of interest, such as a beating heart. Sensors 30 and 40 are shown as being approximately the same distance from human body object 10. However, this need not be the case. Sensors 30 and 40 may be stacked on top of one another so that one is further distant from body surface 27 as shown in FIG. 2 and represented by sensors 30' and 40' wherein sensor 30' is closer to object 10 than sensor 40'. In any case, as will become fully evident below, the exact arrangement or positioning of the sensors relative to the body of interest can vary in accordance with the invention. At this point, it is only important to note that capacitive-type sensors are being employed.

Figure 3:
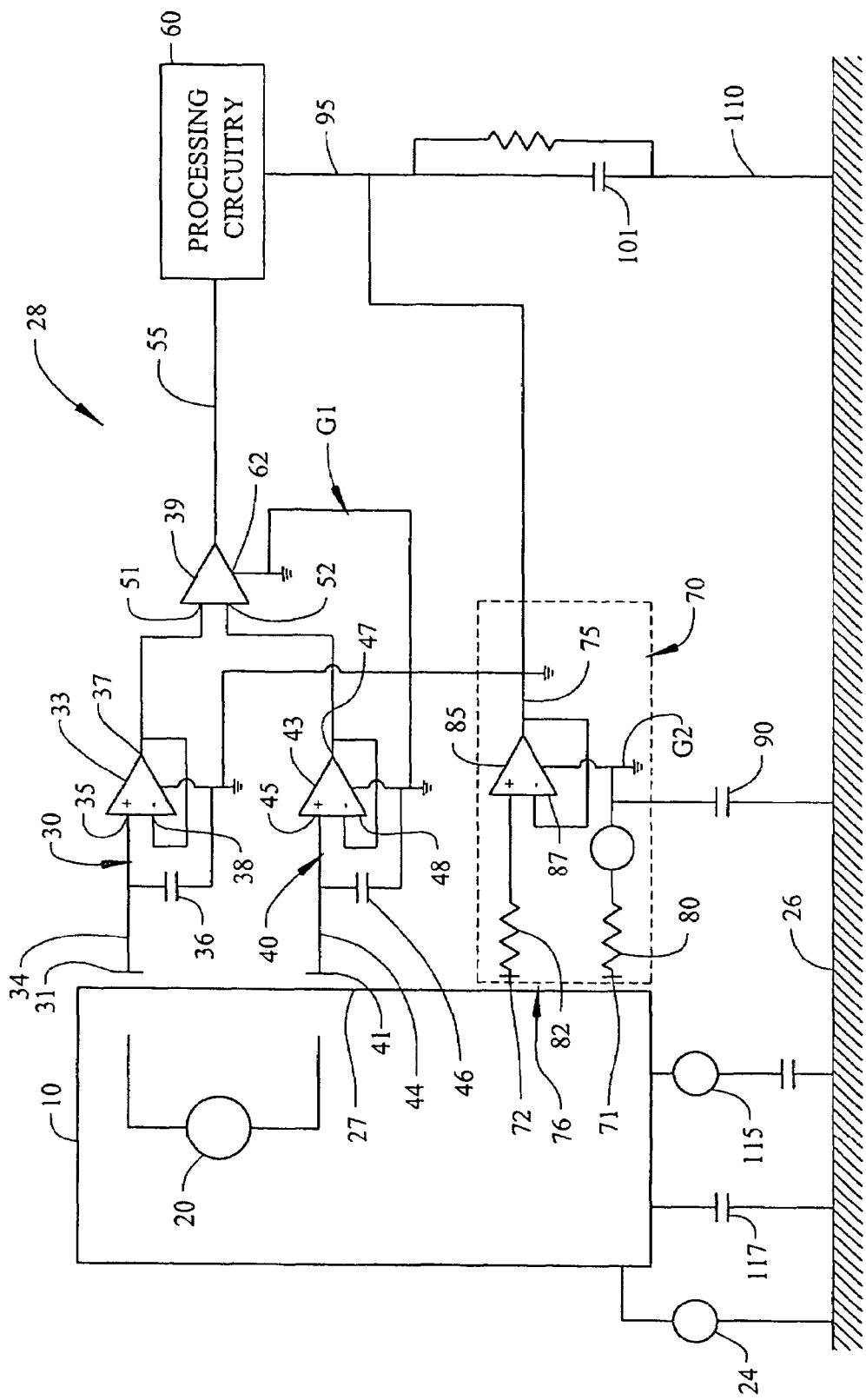
FIG. 3 is a diagram of a circuit designed to take an electrocardiogram of a human body using capacitive sensors and which incorporates circuit elements designed to reduce the negative effects of the background static potential according to a first preferred embodiment of the invention.
Figure 4:
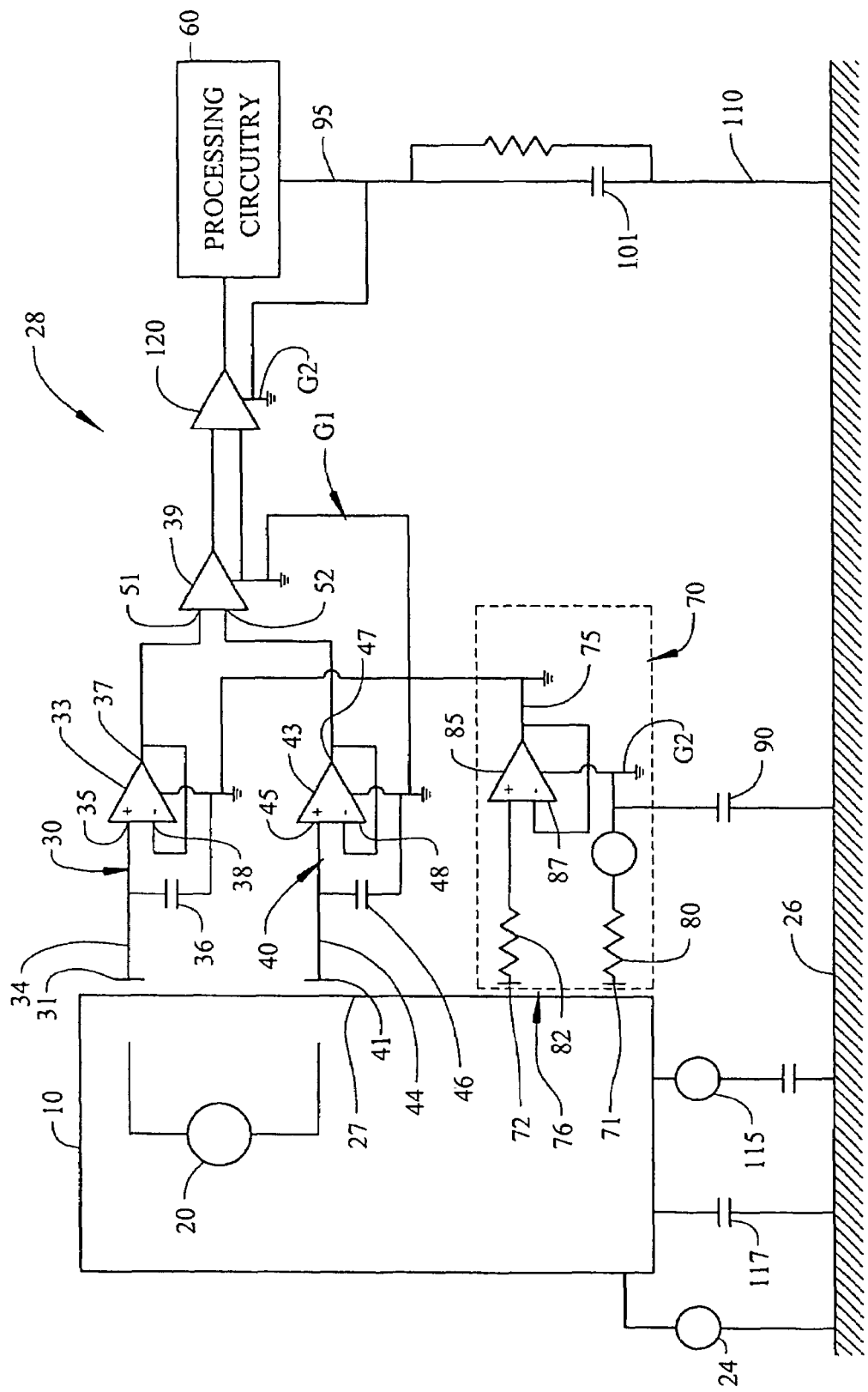
FIG. 4 is a diagram of a circuit designed to take an electrocardiogram of a human body using capacitive sensors and which incorporates circuit elements designed to reduce negative effects of background static potential according to a second preferred embodiment of the invention.

With reference to FIG. 3, sensor system 28 is tied to static potential 24 of object 10 so that the changes in static potential 24 are transferred to a common ground G1. Typically, a battery terminal is utilized as common ground although, when describing the present invention, one of the voltage circuits defines common ground G1. In the preferred embodiment, first sensor 30 is placed in close proximity to object 10. Sensor 30 includes a capacitive electrode 31 and an amplifier 33. An electrical connection 34 is provided between electrode 31 and non-inverting terminal 35 of amplifier 33. Of course, amplifier 33 is powered by a source, such as a battery (not shown). Electrical power travels to amplifier 33 and then to common ground G1. A capacitive connection 36 is shown in the path between electrode 31 and both non-inverting amplifier input 35 and common ground G1. Also, an output 37 of amplifier 33 branches into two lines. The first line is fed back to inverting terminal 38 of amplifier 33 to produce a high impedance voltage follower and thus ensures amplifier 33 stays in its operating range. The other branch of the output is connected to a differential amplifier 39.

Second sensor 40 is also placed in close proximity to object 10. Sensor 40 includes a capacitive electrode 41 and an operational amplifier 43. An electrical connection 44 is provided between electrode 41 and non-inverting terminal 45 of operational amplifier 43. Of course amplifier 43 is powered by a source, such as a battery (not shown). Electrical power travels to amplifier 43 and then to common ground G1. A capacitive connection 46 is shown between the path in electrode 41 and both non-inverting amplifier input 45 and common ground G1. Also, an output 47 of amplifier 43 branches into two lines. The first line is fed back to an inverting terminal 48 of amplifier 43 to produce a high impedance voltage follower and thus ensures amplifier 43 stays in its operating range. The other branch of output 47 is connected to differential amplifier 39.

Differential amplifier 39 takes two signals, one at each input 51 and 52 from two sensors 30 and 40, finds the difference between signals and generates an output signal at output 55 proportional to that difference. Output 55 connects with control and processing circuitry 60 that further processes the output signal. Power is supplied to differential amplifier 39 from the battery. Amplifier 39 has a terminal 62 connected to the same common ground G1 as sensor amplifiers 33 and 34.

A ground-sensing circuit 70 is also provided in sensor system 28. Ground-sensing circuit 70 includes a nominal ground electrode or first connection 71 and a ground-sensing electrode or second connection 72. An output 75 of the ground-sensing circuit 70 drives common ground G1 of sensors 30 and 40 used to measure the signal of interest. The result is to minimize the static induced potential difference across inputs 31 and 41 of sensors 30 and 40. As shown, nominal ground electrode 71 includes an electrical connector that forms a connection to object 10 at a location 76 where the signal of interest formed by voltage source 20 is expected to be small. The connection is preferably a capacitive-type connection but may be a resistive-type connection. The resistive-type connection can be made by a weak resistive connection, such as by a dry metal electrode on the skin of a test subject. In such an arrangement the capacitive connection would be implemented via a conducting fabric or a simple conducting surface that is electrically insulated from the skin. Preferably the connection between nominal ground electrode 71 and common ground G2 has a low electrical impedance.

Ground sensing electrode 72 is also connected to object 10 where the signal of interest formed by voltage source 20 is expected to be small. Ground sensing electrode 72 is preferably placed near nominal ground electrode 71. Like nominal ground electrode 71, ground sensing electrode 72 may be a capacitive or resistive-type electrode. For instance, the ground connection can be made by a weak resistive connection, such as by a dry metal electrode on the skin of a test subject. The connection may also be a capacitive connection, such as via a conducting fabric or a simple conducting surface that is electrically insulated from the skin.

In contrast to nominal ground electrode 71 that measures a nominal ground, ground sensing electrode 72 has an electrical connection, through a resistor 82, to the input of a high impedance amplifier 85. Preferably the impedance of high impedance amplifier 85 is on the order of a terra ohm. The function of ground-sensing electrode 72 is to measure static potential 24 of object 10. The output of high impedance amplifier 85 is fed back to its inverting input terminal 87 and is also connected to common ground G1 of the sensors 30 and 40 used to measure the signal of interest.

The ground-sensing circuit 70 can be better understood when one considers that, ideally, a battery common ground G2 of a ground-sensing circuit 70 would be the same potential 24 as object 10. However, because the connection of the nominal ground electrode 71 to object 10 is poor, battery common ground G2 will not, in general, be that of body potential 24, but rather at some intermediate potential between object 10 and other objects around it. For instance, consider a sudden change in static potential 24, e.g., ΔV static of 20 volts and a change of the voltage of battery common ground G2 of the ground-sensing circuit 70 of 15 volts. The reason why battery common ground G2 voltage differs from the ΔV static 24 is because of the potential divider network formed by the impedance of the common ground G2 to object 10, and capacitive coupling 90 of ground sensor 70 to its local environment 26 which is taken to be a zero voltage relative to body potential 24. As noted, ground-sensing electrode 72 is connected to high-impedance amplifier 85 and so the potential represented at the input to ground-sensing circuit 70 is very close to ΔV static, say 19.9 volts in the example. Amplifier 85 is connected in a voltage follower configuration, and so the output of ground-sensing circuit 70 is 19.9 volts minus 15 volts or 4.9 volts relative to its nominal ground of 15 volts. As a result, the output 25 of ground-sensing circuit 70 is 19.9 volts, very close to ΔV static of 20 volts.

The output 75 of ground-sensing circuit 70 is preferably used to control the common ground G1 for other sensors 30 and 40 used to measure the biological potential signal of interest. Common ground G1 can also be used to drive the ground point of subsequent filtering and data acquisition stages, such as processing circuitry 60, thereby allowing such circuitry 60 to have a large electric coupling to their environment than would otherwise be possible. Note output 75 from ground-sensing circuit 70 going to the ground point 95 of circuitry 60. For example, a battery powered acquisition system placed on a desk will typically be at significantly different instantaneous static potential than that on a human body within one meter of it. Such a large difference can push the sensor output outside the dynamic range of the acquisition system processing circuitry 60 and introduce artifact effect signals and noise. By driving the ground point 95 of the acquisition system processing circuitry 60 via output 75 of ground system circuit 70, such problems and artifact signals or noise can be significantly reduced. This capability enables capacitive electrodes to be coupled to recording systems having processing circuitry 60 not located on the object 10.

The ground-sensing circuit 70 is able to produce a potential that matches the change in static potential 24 very closely, provided the voltage drop across nominal ground electrode 71 is less than the output voltage that can be produced by ground-sensing circuit 70. This output range can be increased by additional amplifiers and larger voltage rails but, in general, a range of −10 volts to +10 volts is adequate for use on a clothed human body.

It should be further appreciated that the performance of ground-sensing circuit 70 can be improved, or the requirements on it alleviated, by reducing the generation of static electricity by sensors 30 and 40 rubbing on skin and/or by reducing capacitive coupling 90 of the system to the local environment ground 26. A reduction in static electricity generation can be minimized by coating sensors 30 and 40. Also, sensors 30 and 40 can be separated from object 10 to minimize direct rubbing.

Capacitive coupling of the system to its environment can be reduced by reducing system size. For example, one could power both ground-sensing circuit 70 and sensors 30 and 40 themselves from a single battery or power supply. To do this, the power source would employ inductive or capacitive isolation to drive separate circuits that are de-coupled from each other at the frequency of interest. The system size may also be reduced by using sensor components optimized to reduce power, thereby allowing the use of a very small battery. Additionally, sensors 30 and 40 could be used that only swing voltage from zero to either a positive or negative voltage. This reduces the number of cables linking sensors 30 and 40 to the rest of the system from three to two, thus reducing the capacitive coupling.

Capacitive coupling of the system to its environment could also be reduced by improving the performance of ground-sensing circuit 70 by reducing the requirements on it. For example, one or more of the components could be located off of or spaced from object 10 and linked via a wireless link (not shown). Such a link can transmit analog or digital information and therefore allow data acquisition from a data storage and data display system to be located off of object 10. Such an approach removes an effective capacitance 101 coupling sensor system 28 to the environment.

In operation of sensor system 28, occasionally a portion of object 10 where ground-sensing circuit 70 is attached is also coupled in a low impedance manner to the ground of the data acquisition processing circuitry 60. Such a ground may occur if the processing circuitry 60 is housed in a conducting case that touches object 10. Also, processing circuitry 60 may be used to collect data from another sensor or system which establishes a low impedance contact with object 10. When such a ground connection occurs, current flows down the common ground G1 of ground-sensing circuit 70 to processing circuitry 60 and back to object 10. Such a current can be reduced to negligible levels by modifying ground-sensing circuit 70 and sensor system 28 as shown in FIG. 4.

More specifically, in FIG. 4 the output of ground-sensing circuit 70 is not directly connected to ground 95 of processing circuitry 60 as previously shown in FIG. 3. Instead, ground 95 of processing circuitry 60 is connected to a common ground G2. The output of amplifier 39 is not connected to the control and processing circuitry 60. Instead, the output from yet another differential amplifier 120, the inputs for which are common ground G1 and the output from the first differential amplifier 39, is connected to the control and processing circuitry 60. The ground for the differential amplifier 120 is common ground G2.

As seen in FIGS. 3 and 4, a common mode source 115, such as a 60 Hz AC power line, may be present. Such a source 115 may cause an artifact signal to pass through a weak capacitive coupling (not shown) to object 10 and then through another capacitive coupling 117 between object 10 and ground 26. The sensitivity of sensor system 28 is reduced in a manner corresponding to that set forth above to compensate for this artifact signal.

Further improvements may also be made to the system. For example, the current flow to object 10 in all circumstances may be reduced by placing resistors 80 and 82 in series with electrodes 71 and 72. Resistors, not shown, may be also placed in series with coupling capacitive-type electrodes 31 and 41, the inputs to amplifiers 33 and 43, and any of the guard circuits that have appreciable coupling to object 10. The addition of resistors in these paths limits the current flowing to object 10 in case of faults with sensors 30 and 40. This potential feature is particularly useful in case switch sensors are used to measured signals from a human body.

To reduce the relative effect of variations in the static field, note that the distance of sensors 30' and 40' from object 10 can be increased as shown in FIG. 2, which has the effect of adding a series capacitance and reducing the dependence of the coupling efficiency on the electrode capacitance. Optionally, a wet region between sensors 30 and 40 and object 10 may be provided with a mildly conducting fluid in order to reduce variations in the electrical properties of the outer skin.

Figure 5:
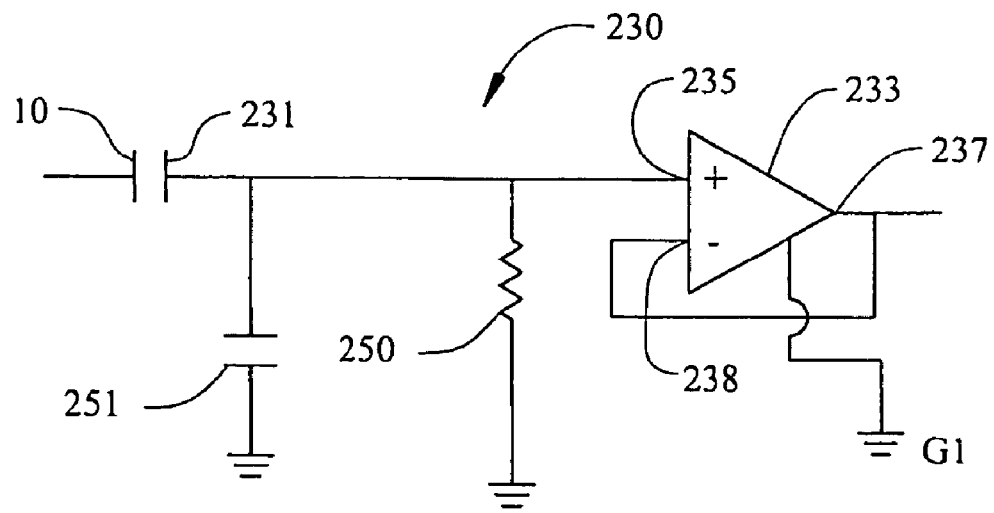
FIG. 5 is a diagram showing a simple capacitive sensor circuit according to a preferred embodiment of the invention.

In another embodiment that may be used alone or in conjunction with the previous embodiments, the circuit for the sensor itself may be modified so that it is less susceptible to differences in coupling of the electrode to the object 10. FIG. 5 shows a simple form of a sensor 230. Sensor 230 includes a capacitive electrode 231 having a value Cin connected to object 10 and an operational amplifier 233. An electrical connection is provided between electrode 231 and a non-inverting terminal 235 of operational amplifier 233. Of course, amplifier 233 is powered by a source, such as a battery (not shown). Electrical power travels to amplifier 233 and then to the common ground G1. A connection is provided from output 237 to an inverting terminal 238 to produce a high impedance voltage follower. A resistor 250 represents the combination of the amplifier input resistance and shunt resistance added to amplifier 233 to stabilize amplifier 233 with respect to its bias current. Capacitor 251 represents the amplifier input capacitance value CA. Amplifier 233 and the value of resistor 250 are preferably selected so that the overall range is approximately from 1 Hz to 50 Hz and the effect of resistor 250 on the circuit transfer function is negligible. In the circuit's functional form, the value of resistor 250 can be neglected, and the fraction of the signal N coupled to amplifier input 235 is given by the ratio $\eta = Cin/(Cin+CA)$.

To this point, it should be realized that the combination of resistor 250 and capacitors 231 and 251 produce a high-pass filter effect on signals detected from object 10. The high pass action has RC time constant $\tau = R(Cin+CA)$ and corner frequency $\omega c = 1/\tau$. A phase shift is introduced between signals from object 10 and signals measured by amplifier 233 by the high pass action of the combination of resistor 250 and capacitors 231 and 251, even at frequencies above $\omega c$. In applications involving two sensors, such as those shown in FIGS. 3 and 43, each sensor has a slightly different corner frequency. This is due to variations in C, Cin and R in both circuits, the values for which are often difficult to control. Consequently there exists a different phase shift for each sensor. Any mismatch in the phase shifts for the two sensors limit the performance of amplifier 39 to take a high common mode difference. To minimize this effect, values of R and C are preferably selected such that $\omega c$ is less than 40 mHz.

Figure 6A:
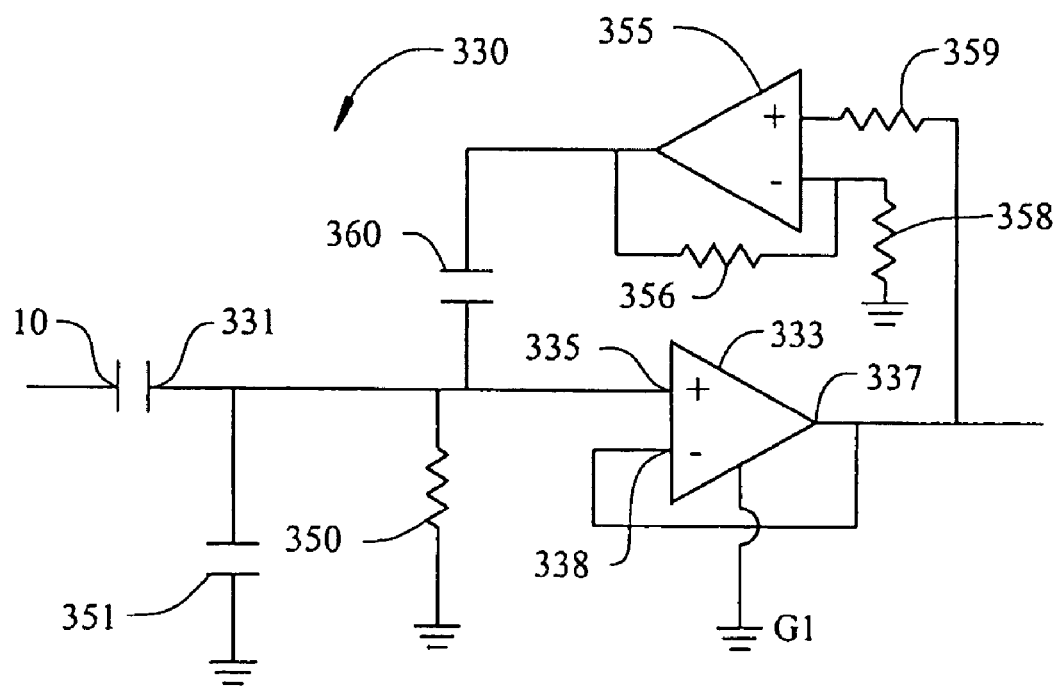
FIG. 6A is a diagram showing a more complex version of a capacitive sensor circuit including a negative capacitance circuit.

As shown in FIG. 6A, there is a modified form of sensor 330 including a feedback network that has improved properties in that $\eta$ is less susceptible to changes in Cin. In this circuit, sensor 330 includes a capacitive electrode 331 having a value Cin and an amplifier 333. An electrical connection is provided between electrode 331 and a non-inverting terminal 335 of amplifier 333. Of course, amplifier 333 is powered by a source such as a battery (not shown). Electrical power travels to amplifier 333 and then to the common ground G1. A connection is provided from output 337 to inverting terminal 338 to produce a high impedance voltage follower. A resistor 350 represents the combination of the amplifier input resistance and shunt resistance added to amplifier 333 to stabilize it with respect to its bias current. Capacitor 351 represents the amplifier input capacitance value CA, including residual stray capacitances. Additionally, current is fed back into amplifier terminal 335 to cancel the current that flows into amplifier 333. Specifically, output 337 of amplifier 333 travels through an amplifier 355. The output (not separately labeled) of amplifier 355 is fed to an inverting input (not separately labeled) of amplifier 255 through a resistor 356 having a value of RF. The inverting input of amplifier 355 is further connected to ground through resistor 358. A resistor 359 is provided at the non-inverting terminal (not separately labeled) of amplifier 355 and a capacitor 360, having the value CF, is also provided in the feedback loop. This feedback has the effect of reducing the effective value of CA and constitutes a negative impedance converter. The efficiency of such a circuit is given by:

$$\eta = V_{out}/V_{in} = Cin/(Cin+CF+CA-G*CF)$$

where G is the gain of the feedback path and can be adjusted via feedback resistor 356. G is tuned to equal $1+Ca/CF$, in which case $\eta = 1$ and, more importantly, does not depend on the value of Cin, i.e., is less affected by variations in Cin. Using this approach, 99.9% cancellation of the static signal can be achieved between capacitive sensors, even through clothing. Both the capacitance of the amplifier 333 and the residual stray capacitance of the system can be controlled in this manner.

Figure 6B:
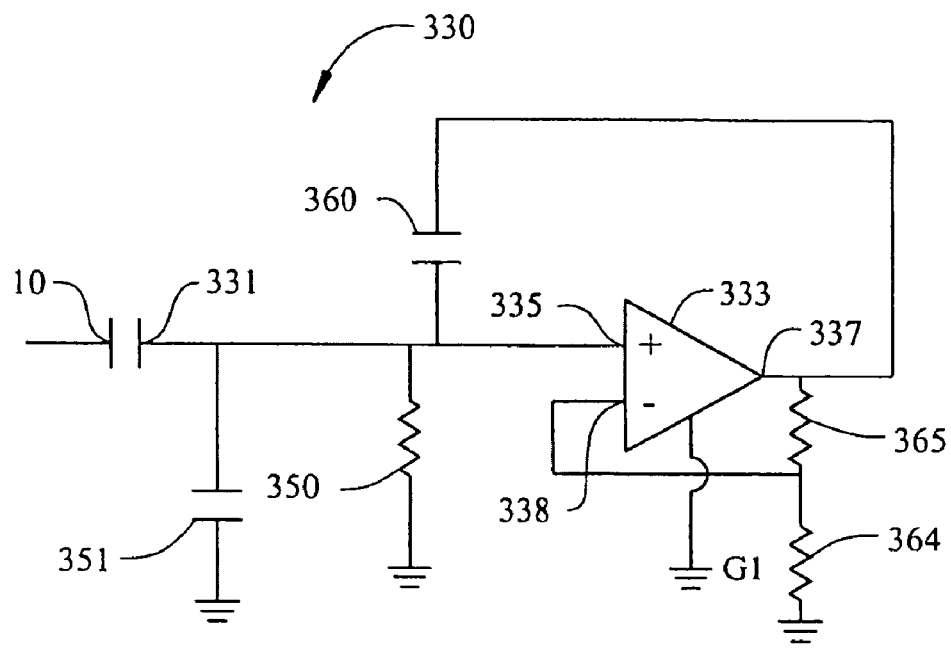
FIG. 6B is a diagram showing another more complex version of a capacitive sensor circuit including a negative capacitance circuit.

FIG. 6B shows a modified form of the sensor 330 shown in FIG. 6A. In FIG. 6B, the feedback loop still includes a capacitor 360. However, the amplifier 355 and its associated resistors 356, 358 and 359 are no longer present. Instead, a passive feedback loop from the output 337 of amplifier 333 travels back to the inverting input 338 of amplifier 333. Additionally provided are resistors 364 to ground and a resistor 365 located in the feedback loop. The passive gain of the feedback loop is therefore set by the ratio of the value RG of resistor 364 and RF of resistor 365. For this circuit, the relationship between the gain and the values RF and RG are set by the following equation:

$$Gain = 1+CA/CF = 1+RF/RG.$$

Figure 7:
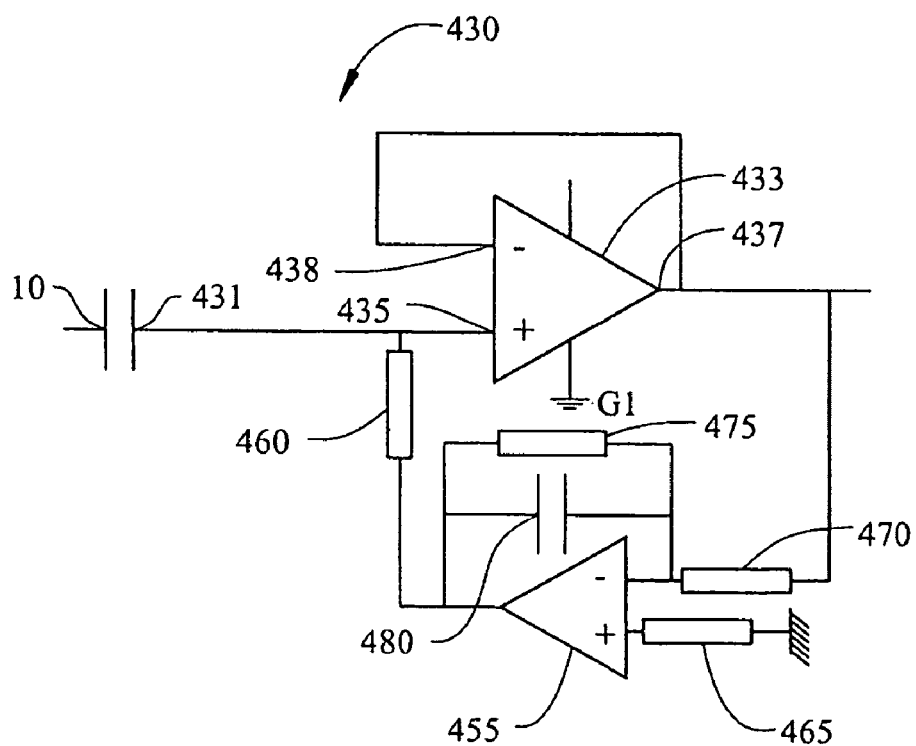
FIG. 7 is a diagram showing a capacitive sensor circuit including DC offset compensation low pass filtered feedback.

Turning now to FIG. 7, there is shown a version of the circuit which embodies a DC offset compensation. The sensor 430 includes a capacitive electrode 431 connected to object 10. An electrical connection is provided between electrode 431 and a non-inverting terminal 435 of an operational amplifier 433. Of course, amplifier 433 is powered by a source, such as a battery (not shown). Electrical power travels to amplifier 433 and then to the common ground G1. A connection is provided from output 437 to inverting terminal 438 to produce a high impedance voltage follower. A feedback circuit is provided through an amplifier 455. A bias resistor 460 is provided between the output of the feedback circuit and non-inverting terminal 435. A resistor 465, having a value R3, is located between non-inverting terminal (not labeled) of amplifier 455 and ground G1. Another resistor 470, having a value R3, is located at the non-inverting terminal (not separately labeled) of amplifier 455. A resistor 475, having a value R2, and a capacitor 480, having a value C2, are provided in parallel between the output of amplifier 455 and its inverting input. With this arrangement, a low pass filtered version of the output voltage is fed back into the input through bias resistor 460. The values R2, R3 and C2 are chosen to set the frequency of the low pass filter, particularly to a frequency less than the frequency of the required band width.

Figure 8:
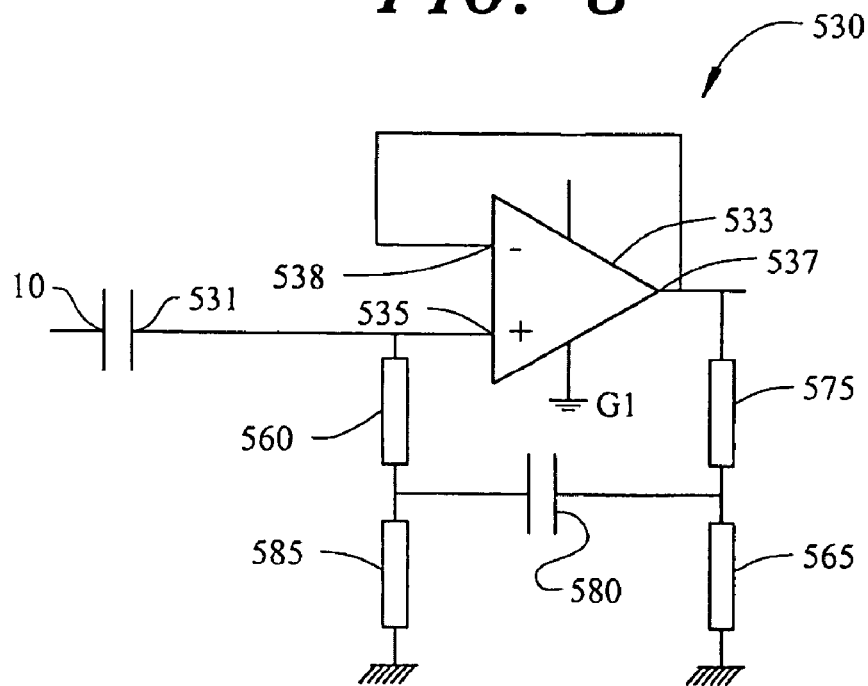
FIG. 8 is a diagram showing a capacitive sensor circuit with a high pass filter.

Turning now to FIG. 8, a sensor 530 is shown including a capacitive electrode 531 connected to object 10 and an operational amplifier 533. An electrical connection is provided between electrode 531 and a non-inverting terminal 535 of operational amplifier 533. Of course, amplifier 533 is powered by a source, such as a battery (not shown). Electrical power travels to amplifier 533 and then to the common ground G1. A connection is provided from an output 537 to an inverting terminal 538 to produce a high impedance amplifier. A feedback circuit is provided through a resistor 560 having a value R1. In addition, resistors 565 and 575 are provided having values R3 and R2, respectively. Between resistors 565 and 575, an output connects an electrical signal to the input of resistor 560 through a capacitor 580 having a value C2. Finally, a resistor 585 is optionally provided to ground and creates a path for the bias current. The capacitor 580 constrains the bias current to flow through resistor 560 and resistor 585. This version of the circuit 530 embodies partial guarding of bias resistor 560 to lower the effective frequency of the high pass filter formed by the resistor/capacitor combination. The ratio of R2 and R3 sets the ratio of the extension to low frequency of the RC filter in accordance with the equation shown below:

$$R1C1\ apparent = R1C1/[1-R3/(R2+R3)*Rx/(Rx+R2*R3/(R2+R3))]$$

It should be noted that capacitor 580 is included to allow for the circuit to be employed with other circuitry. If no other circuitry is used, of course, this capacitor could be replaced with a short.

Figure 9:
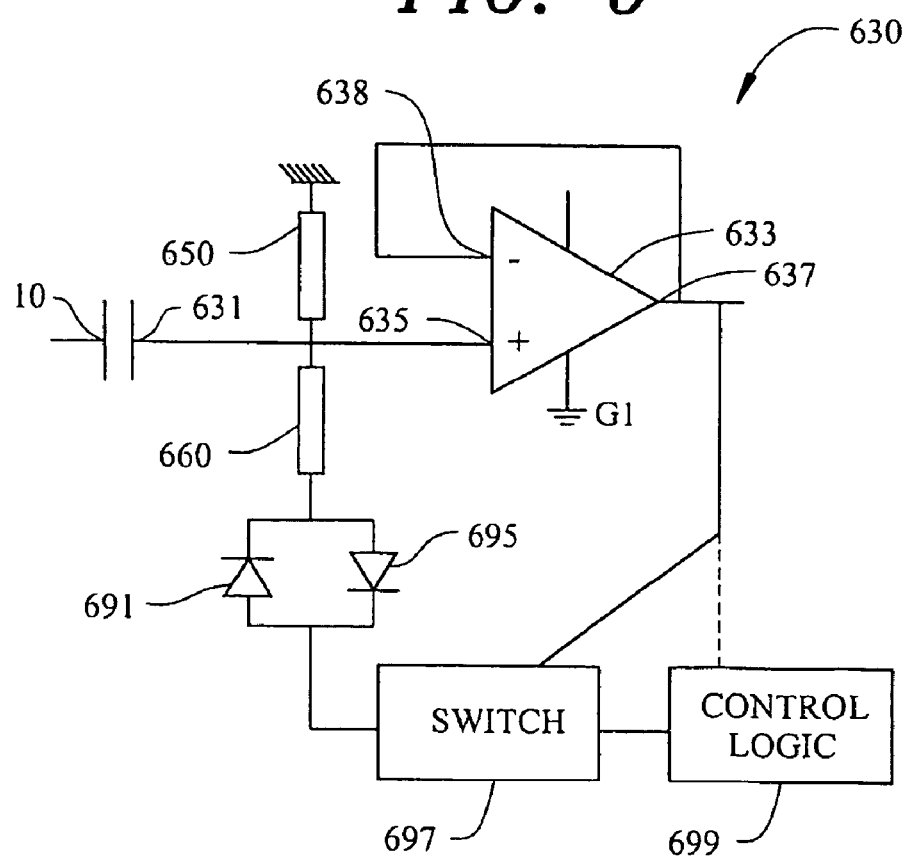
FIG. 9 is a diagram showing a capacitive sensor circuit with an active saturation recovery feature.

Turning to FIG. 9, a sensor 630 is shown including a capacitive electrode 631 connected to object 10 and an opeation amplifier 633. An electrical connection is provided between electrode 631 and a non-inverting terminal 635 of operational amplifier 633. Of course, amplifier 633 is powered by a source, such as a battery (not shown). Electrical power travels to amplifier 633 and then to the common ground G1. A connection is provided from an output 637 of amplifier 633 to an inverting terminal 638 to produce a high impedance follower. Additionally, a resistor 650, having a value of R1, is provided to ground. A feedback circuit is provided through a resistor 660 having a value of R2. A pair of diodes 691 and 695 are provided as part of a diode package. Leading to the diode package is a switch 697 controlled by a control logic 699. With this arrangement, circuit 630 constitutes an active saturation recovery circuit. Circuit 630 detects when the output voltage strays outside of its normal operating range. Upon detection of this event, the input circuit is driven with feedback to zero voltage. The feedback gain is preferably −1000, but could range from −1 to −10,000. This feedback is applied for a fixed period of time after the circuit recovers below the operating voltage range. During normal operation, a guard signal is fed to the bottom of the diode package to maintain high input impedance.

Based on the above, it should be readily apparent that each of the embodiments of the invention described above advantageously employs capacitive sensors for non-invasive measurements, while providing additional circuitry to effectively reduce artifact noise signals. Although described with reference to preferred embodiments of the invention, it should be readily understood that various changes and/or modifications could be made to the invention without departing from the spirit thereof. For example, instead of using switch 697 and control logic 699, the feedback circuit of FIG. 8 could be constructed using passive components. Diodes and resistors could be configured to switch diodes 691 and 695 between ground and guard (i.e., output of 637 of amplifier 633). In general, the invention is only intended to be limited by the scope of the following claims.

We claim:

1. A sensor system for measuring an electric potential signal of interest generated by an object comprising:
    a first signal sensor including a local ground connection, an input and an output;
    processing circuitry including an input connected to said output of the first signal sensor and the local ground connection;
    a ground sensor including:
        a first ground electrode;
        a second ground electrode, and
        a high impedance amplifier with a DC supply, a ground connection connected to both said first ground electrode and a universal ground, an input connected to said second ground electrode and an output connected to the local ground connection of said first signal sensor, whereby a voltage of the local ground connection of the first signal sensor is forced to be substantially the same as a voltage presented by the object at said ground sensor so as to reduce an effect of a change in static potential on the signal of interest.

2. The sensor system according to claim 1, wherein said first signal sensor further includes:
    a capacitive-type electrode; and
    an amplifier with a DC supply, wherein the input is connected to the capacitive-type electrode.

3. The sensor system according to claim 2, further comprising: a feedback network electrically connected to the first signal sensor.

4. The sensor system according to claim 3, wherein said feedback network includes an amplifier and a series capacitor, and wherein a gain of the amplifier of the feedback network is set to 1 plus an input capacitance of the amplifier of the first signal sensor divided by a value of the series capacitor of the feedback network.

5. The sensor system according to claim 1, further comprising:
    a second signal sensor including an input and an output;
    a differential amplifier including a first input connected to the output of said first signal sensor, a second input connected to the output of said second signal sensor and an amp output providing the signal of interest which is proportional to the difference between a signal from the first signal sensor and a signal from the second signal sensor.

6. The sensor system according to claim 5, wherein said second signal sensor further includes:
a capacitive-type electrode; and
an amplifier with a DC supply, wherein the input of the second signal sensor is connected to the capacitive-type electrode.

7. The sensor system according to claim 1, further comprising:
a capacitor electrically disposed between the electrode and the high impedance amplifier.

8. The sensor system according to claim 1 wherein the first signal sensor constitutes a capacitive sensor such that, during use of the sensor system, the first signal sensor is entirely spaced from the object.

9. A sensor system for measuring an electric potential signal of interest generated by an object comprising:
a first signal sensor including a local ground connection, an input and an output;
processing circuitry including an input connected to said output of the first signal sensor and the local ground connection;
a ground sensor including a first ground electrode, and a second ground electrode;
a second signal sensor including an input and an output; and
a differential amplifier including a first input connected to the output of said first signal sensor, a second input connected to the output of said second signal sensor and an amp output providing the signal of interest which is proportional to the difference between a signal from the first signal sensor and a signal from the second signal sensor, whereby a voltage of the local ground connection of the first signal sensor is forced to be substantially the same as a voltage present at said second ground electrode so as to reduce an effect of a change in static potential on the signal of interest.

10. The sensor system according to claim 9, wherein said first signal sensor further includes:
a capacitive-type electrode; and
an amplifier with a DC supply, wherein the input is connected to the capacitive-type electrode.

11. The sensor system according to claim 10, further comprising: a feedback network electrically connected to the first signal sensor.

12. The sensor system according to claim 9, wherein said second signal sensor further includes:
a capacitive-type electrode; and
an amplifier with a DC supply, wherein the input of the second signal sensor is connected to the capacitive-type electrode.

13. The sensor system according to claim 9, wherein said ground sensor further includes:
a high impedance amplifier with a DC supply, a ground connection connected to both said first ground electrode and a universal ground, an input connected to said second ground electrode and an output connected to both the local ground connection of said first signal sensor and said second ground electrode.

14. The sensor system according to claim 13, further comprising:
a capacitor electrical disposed between the electrode and the high impedance amplifier.

15. The sensor system according to claim 9 wherein, during use of the sensor system, the first signal sensor is entirely spaced from the object.

16. A sensor system, for measuring an electric potential signal of interest generated by an object comprising:
a first signal sensor including a local ground connection, an input, an output, a capacitive type electrode, and an amplifier with a DC supply, wherein the input is connected to the capacitive type electrode;
processing circuitry including an input connected to said output of the first signal sensor and the local ground connection;
a ground sensor including a first ground electrode and a second ground electrode; and
a feedback network electrically connected to the first signal sensor, wherein said feedback network includes an amplifier and a series capacitor, and wherein a gain of the amplifier of the feedback network is set to 1 plus the input capacitance of the amplifier of the first signal sensor divided by a value of the series capacitor of the feedback network and whereby a voltage of the local around connection of the first signal sensor is forced to be substantially the same as the voltage presented by the object and said around sensor so as to reduce an effect of a change in static potential on the signal of interest.

17. A method of measuring an electric potential signal of interest generated by an object comprising:
sensing the electric potential signal through a capacitive-type sensor including a local ground connection, an input and an output;
sensing a ground signal though a ground sensor having first and second ground electrodes;
reducing an effect of a change in a potential on the signal of interest by causing a voltage present at the local ground connection of the capacitive-type sensor to be substantially the same as a voltage present at said second ground electrode; and
providing a feedback signal from a feedback network, including an amplifier and a series capacitor, electrically connected to the capacitive-type sensor, with a gain of the amplifier of the feedback network being set to 1 plus an input capacitance of an amplifier of the capacitive-type sensor divided by a value of the series capacitor of the feedback network.

* * * * *